United States Patent
Seitz et al.

(10) Patent No.: US 10,758,124 B2
(45) Date of Patent: Sep. 1, 2020

(54) DEVICE AND METHOD FOR DISTANCE DETERMINATION AND/OR CENTERING USING CORNEAL REFLECTIONS

(71) Applicant: Rodenstock GmbH, Munich (DE)

(72) Inventors: Peter Seitz, Munich (DE); Markus Tiemann, Munich (DE); Gregor Esser, Munich (DE); Anne Seidemann, Munich (DE); Werner Mueller, Oetisheim (DE)

(73) Assignee: Rodenstock GmbH, Munich (DE)

( * ) Notice: Subject to any disclaimer, the term of this patent is extended or adjusted under 35 U.S.C. 154(b) by 346 days.

(21) Appl. No.: 15/550,683

(22) PCT Filed: Jan. 26, 2016

(86) PCT No.: PCT/EP2016/000133
§ 371 (c)(1),
(2) Date: Aug. 11, 2017

(87) PCT Pub. No.: WO2016/128112
PCT Pub. Date: Aug. 18, 2016

(65) Prior Publication Data
US 2018/0042477 A1   Feb. 15, 2018

(30) Foreign Application Priority Data
Feb. 13, 2015   (DE) .......... 10 2015 001 874

(51) Int. Cl.
*A61B 3/10*   (2006.01)
*A61B 3/15*   (2006.01)
(Continued)

(52) U.S. Cl.
CPC ............ *A61B 3/154* (2013.01); *A61B 3/0008* (2013.01); *A61B 3/14* (2013.01); *A61B 3/152* (2013.01); *G02C 13/005* (2013.01)

(58) Field of Classification Search
CPC ....... A61B 3/0075; A61B 3/0083; A61B 3/12; A61B 3/145; A61B 3/152; A61B 3/154; A61B 3/0008; A61B 3/14; G02C 13/005
(Continued)

(56) References Cited

U.S. PATENT DOCUMENTS 7,740,355 B2 *  6/2010  Sessner ................ G02C 13/005
                                                            351/204
2006/0110008 A1   5/2006  Vertegaal et al.

FOREIGN PATENT DOCUMENTS

DE   102004053629 A1   5/2006
DE   102005038218 A1   2/2007
(Continued)

OTHER PUBLICATIONS

German Patent Office, PCT International Search Report issued for PCT/EP2016/000133, 11 pgs., dated Apr. 22, 2016.
(Continued)

*Primary Examiner* — William R Alexander
*Assistant Examiner* — Henry A Duong
(74) *Attorney, Agent, or Firm* — Schiff Hardin LLP

(57) ABSTRACT

A device for determining the distance of an eye of a user from the image capturing device is disclosed. The device includes a lighting device that is arranged at a specified position relative to the image capturing device and is designed to generate at least one specular light reflection, which has a linear portion, on the cornea of the eye of the user. The device also includes an image capturing device designed to capture at least one image of the specular light reflection in the region of the cornea of the at least one eye of the user. A distance determining device is designed to ascertain data relating to the distance between two specified points of the light reflection and the curvature of the at least one linear portion of the light reflection in the captured
(Continued)

Figure 1:
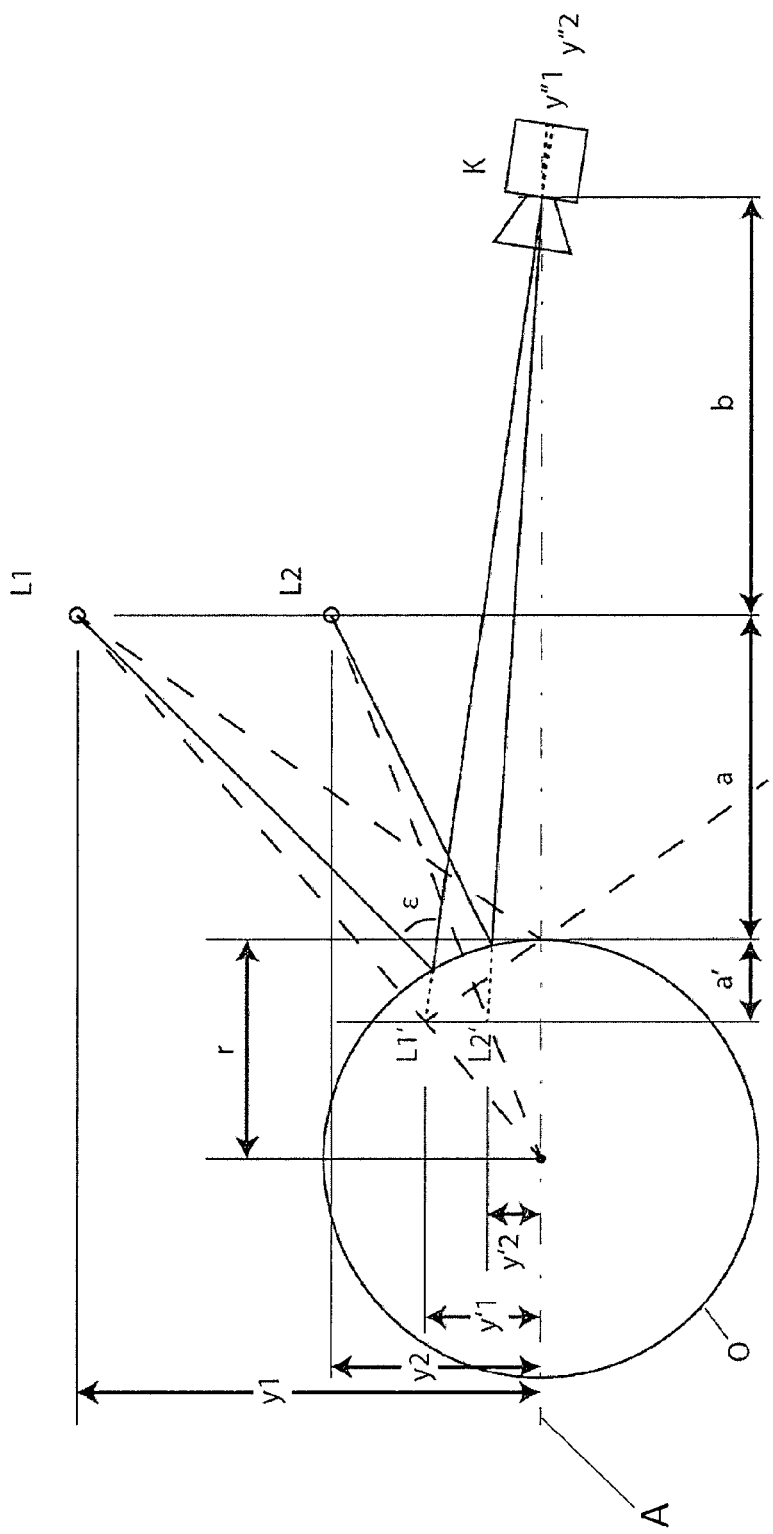

image and the distance of the eye from the image capturing device.

17 Claims, 8 Drawing Sheets

(51) Int. Cl.
*G02C 13/00* (2006.01)
*A61B 3/14* (2006.01)
*A61B 3/00* (2006.01)

(58) Field of Classification Search
USPC .......................................................... 351/208
See application file for complete search history.

(56) References Cited

FOREIGN PATENT DOCUMENTS

| | | |
|---|---|---|
| EP | 2653094 A1 | 10/2013 |
| GB | 2442621 A | 4/2008 |
| WO | WO-2008/009355 A1 | 1/2008 |
| WO | WO-2014/103646 A1 | 7/2014 |

OTHER PUBLICATIONS

German Patent Office, Examination Report issued for DE 102015001874.4, 12 pgs., dated Sep. 25, 2015.

\* cited by examiner

DEVICE AND METHOD FOR DISTANCE DETERMINATION AND/OR CENTERING USING CORNEAL REFLECTIONS

TECHNICAL FIELD

The present invention relates to a device comprising an image capturing device and a measuring device for determining the distance of one eye or both eyes of a user from the image capturing device (such as a camera). The device may be a device to determine optical parameters of a user, a device to create stereo images and/or to determine spatial information in three-dimensional space, a device to display contents depending on the position of a user etc. The present invention also relates to a method to determine the distance of one eye or of both eyes of a user from an image capturing device, and to a computer program product to implement the method.

BACKGROUND

For example, video centering devices are known from the prior art that may determine individual or even all parameters of the eyes of a user and/or of the usage position of spectacles or of spectacles frames in front of the eyes of a user by capturing an image of the user, and possibly with the assistance of additional resources. The parameters of the eyes and/or of the usage position include, for example, the interpupillary distance of the user, the face form angle of spectacles or a spectacles frame worn by the user, the spectacle lens inclination, the shape of the spectacles frame, the corneal vertex distance of the system of spectacles and eye, the fitting height of the spectacle lenses etc.

The publication DE 10 2005 003 699 A1 discloses a stereo camera system having two cameras that respectively capture an image of a user with spectacles from different capture directions, from which three-dimensional user data are calculated. Video centering devices with a camera are likewise known which make chronologically offset exposures of the eye area of the of the user to be measured from different viewing angles. The exposures are subsequently oriented relative to one another with the assistance of a reference object in the image (for example a centering clip) so that a stereo camera system is likewise formed. Other solutions use only the projection captured with a camera in a view of a wearer of a [spectacles] frame on which a centering clip is mounted. Some parameters may be approximately determined via an assumption of values of the corneal vertex distance, an inclination difference between centering clip and mount, and a face form angle.

The parameters of the eyes and/or of the usage position of spectacles or a spectacles frame in front of the eyes of a user, said parameters being determined by means of a video centering device, may on the one hand be considered in the fitting and insertion of spectacles lenses in a spectacles frame; on the other hand, optimizations in the spectacles lens itself may therefore be made in order to adapt it to the wear position in the usage position.

Camera-based devices are also known in which the content on a monitor varies depending on the bearing and/or head position of the user in front of the monitor. An example of a device that is designed to test the visual acuity of a user in which the size of the vision test characters may vary depending on the position of the user is disclosed in DE 10 2014 009 459.

In the above camera-based devices, it is often important to obtain information about the position of an object captured by the camera (for example an eye of a user) relative to said camera, in particular about the distance of the object from the camera.

SUMMARY

It is an object of the invention to provide an improved and simple possibility to determine the distance of one eye or of both eyes of a user from an image acquisition device. An additional object of the invention is to provide an improved and simple possibility of determining optical parameters of a user. These and other objects of the invention are achieved via the subject matters of the independent claims.

A first aspect relates to a device having an image capturing device and a measurement device for determining the distance of at least one eye of a user from the image capturing device (eye-image capturing device distance). The measurement device comprises a lighting device which is arranged at a predetermined position relative to the image capturing device, and which is designed and set up to generate at least one light reflection with an essentially line-shaped or linear or extended segment. The shape or structure of the light source may be known in advance; in particular, the distance between at least two predetermined or provided points of the light source and the shape and/or position of at least one essentially line-shaped segment of the light source may be known in advance. The light source may be a structured light source having multiple individual light sources. The essentially line-shaped segment of the light source may be a straight-line segment, for example.

The image capturing device is designed and set up to capture at least one image of the specular light reflection, or of the reflection of the light source, on the cornea of the examined eye of the user. The image capturing device may comprise one or more cameras that are directed toward the eye area of the user and may capture at least one image in which the specular light reflection on the cornea of the at least one eye is visible.

The measurement device also comprises a distance determination device to determine the eye-image capturing device distance, which may be implemented in a data processing device. The distance determination device is designed to process the at least one image captured by the image capturing device, and to determine data with regard to the distance between the two predetermined or previously known points in the light reflection, and with regard to the curvature of the at least one line-shaped segment of the light reflection in at least one captured image. The distance determination device is also designed to determine the distance of the eye from the image capturing device using the determined data with regard to the distance between the two predetermined points of the light reflection and a curvature of the at least one line-shaped segment of the light reflection. The distance determination device may have a processor or be realized as a corresponding module of a processor or computer. The distance determination device may be realized by means of the correspondingly programmed microprocessor of a mobile computer (for example notebooks, laptops, tablets, smartphones etc.).

In particular, given a known shape and dimension of the light source, the distance of the eye from the image capturing device may be determined using the specular light reflection in at least one image captured by the image capturing device. The shape of the specular light reflection on the cornea in the captured image is thus superordinately dependent on the geometry of the measurement system, and especially on the distance between the image capturing device and the eye. The distance between the image capturing device and the examined eye may consequently be determined using the measured distance between two previously known or predetermined points of the light reflection in the captured image. For example, the previously known or predetermined points of the light reflection may be the end points of the line-shaped segment of said light reflection, such that information about the eye-image capturing device distance may be obtained using the length of the line-shaped segment measured in the image. The predetermined points may also be other points of the light source whose original position in the light source is known.

In order to increase the measurement precision, it is also proposed to likewise take the dependency of the curvature of the line-shaped segment of the light reflection in the captured image on the distance between the image capturing device and the eye into account in the determination of the eye-image capturing device distance. The distance of the eye from the image capturing device is thus determined using data with regard to the distance between two previously known points of the light reflection and the curvature of the at least one line-shaped segment of the light source in the captured image. A simple and precise measurement device to determine the eye-image capturing device distance may thus be realized that is in particular suitable for mobile application.

The lighting device may be designed to generate a respective light reflection on the cornea of each of the two eyes. The image capturing device may be designed to capture at least one image of the two eyes. The distance determination device may be designed to determine the eye-image capturing device distance separately for both eyes of the user. A mean value may be calculated using the determined eye-image capturing device distance. The determined mean value may be output as an eye-image capturing device distance. In addition to this, an angle between the image plane of the image capturing device and the connecting line between the eyes may also be determined from the distances of the two eyes from the image capturing device, from which the head rotation may be determined.

The distance determination device may be designed and provided to automatically and/or manually locate the two predetermined points of the light reflection and the at least one line-shaped segment of the light reflection in the captured image. This localization thereby contains spatial information in the form of coordinates and/or pixels from which the distance determination device determines the data with regard to the distance of the two (or more) predetermined points and the curvature of the line-shaped segment of the light reflection. The localizer may thereby take place precisely at two pixels in each coordinate direction of the two-dimensional exposure, preferably precisely at one pixel, especially precisely at a sub-pixel, for example thus precisely at 1/10 of a pixel. For example, this may take place via application and evaluation of a Gaussian distribution with regard to the optical brightness of the pixel in the captured image.

The distance of the eye from the image capturing device may, for example, be determined using information with regard to the (fixed) relative arrangement of the lighting device relative to the image capturing device, and possibly using additional information with regard to the optical system of the image capturing device (for example magnification etc.). This information may be stored as calibration data in suitable form in a calibration data storage device. The calibration data storage device may be a component of the distance determination device.

The calibration data that are considered in the determination of the eye-image capturing device distance may, for example, contain data with regard to the association of distances between the two predetermined points of the light reflection and with regard to curvatures of the at least one line-shaped segment of the light reflection in the captured image relative to determined distance, or distances determined in advance, of measurement objects from the image capturing device. The calibration data may be obtained using previously known metal objects that are arranged at previously known distances from the image capturing device. The measurement objects may be objects having a reflective spherical surface with previously known curvature radius, for example spherical lenses or balls (made of metal, for example). The curvature radius of the spherical surface is preferably between 7 mm and 10 mm. This area corresponds to the curvature of the human cornea.

The calibration data may be obtained by means of an interpolation of multiple data points. For example, the data points may include measurement values for the distance between two predetermined points of the light reflection and the curvature of the reflection of the line-shaped segment of the light reflection in an image that was captured by the camera of the measurement device to be calibrated. The measurement values may be obtained for multiple different curved measurement objects with known curvatures and for multiple different, previously known measurement object-image capturing device distances. The calibration data may be stored in suitable form, for example tabular, graphical, functional etc.

The light source arranged in the lighting device may be a diffusely radiative light source. The illumination light radiated from the light source preferably has a light wavelength that may be detected quickly and with certainty in the image data, for example automatically via a computer-controlled evaluation. For example, the light source may comprise at least one luminophore tube, LED etc. A pattern displayed on a monitor (for example the monitor of a mobile computer) may likewise serve as a light source.

The shape of the light source, and thus of the light reflection generated by the light source, may in principle be different or largely freely selected, since it is sufficient if the light source has at least one essentially line-shaped, especially straight segment. The light source may thus be a letter, a symbol or a logo. In one example, the light source is comprised of the essentially straight segment. The light source may thus have the shape of a light bar. The two predetermined points between which the distance is measured in the image of the specular light reflection on the cornea may be the end points of the light bar. In this case, the measured distance in the image of the light reflection corresponds to the length of the line-shaped segment or of the light bar. This enables a simple embodiment of the lighting device.

In order to increase the measurement precision, the light source may also have at least two point-shaped or circular segments or areas which mark the points whose distance in the captured image of the specular light reflection on the cornea is measured. The light source may thus, for example, have the shape of a light bar with two essentially point-shaped or circular light dots at both ends of the light bar. The light dots may also be arranged above and below the light bar at a predetermined distance from said light bar.

The light source, and thus the specular light reflection generated by the light source, may likewise have multiple essentially linear or elongated and in particular straight segments, and/or segments with complicated shapes. Data about the shape and/or arrangement of these segments in the captured image may be used in the determination of the eye-image capturing device distance in order to increase the measurement precision.

Additional information and/or parameters can be determined using the determined eye-image capturing device distance. The device may accordingly comprise a data processing device that is designed to determine the additional information and/or parameters under consideration of the determined eye-image capturing device distance.

The device may comprise a scaling factor determination device which is designed to determine a scaling factor using the determined distance of at least one of the eyes from the image capturing device in order to convert a distance measured in an image captured by the image capturing device into an actual distance. The distances measured in the image may, for example, be specified in pixels. The scaling factor may reproduce the conversion of distances measured in pixels in the image into actual distances. It is also possible to determine a separate scaling factor for each eye of the user. If the determined eye-image capturing device distances are different for both eyes, the calculation of the scaling factor may form the basis of a mean value of the two distances.

The distance captured by the image capturing device may, for example, include a capture of both pupils of the user, preferably with the respective specular light reflection on the cornea. The position of the two pupils of the eyes of the user, and the distance of the two pupils in the captured image (in pixels, for example) may be determined using the captured image. Via the determination of the distance of the two pupils in the captured image, and under consideration of the scaling factors for both eyes, the actual distance between the two eyes or between the two pupils in the exposure situation may be determined via an averaging. Given a known fixed point relative to the image capturing device or relative to the camera, the interpupillary distance may be converted with the aid of an eye model for an infinite view. In one example, the fixed point may be the camera objective or a point of the camera objective.

For example, the interpupillary distance of an eye may be determined via the scaling factor in that, for example, the actual interpupillary distance is calculated from an interpupillary distance determined in the captured image by means of the scaling factor.

It is also possible to determine a (for example a second) scaling factor for the frame plane of a spectacles frame or of spectacles worn by a user during the image capture. The frame plane is the plane that is formed by vertical center lines relative to one another of the boxing systems establishing the right and left disc plane of the spectacles frame (see for example DIN 58 208).

The calculation of the scaling factor for the frame plane of a spectacles frame or of spectacles worn by the user may form the basis of a conical vertex distance. The conical vertex distance may, for example, be an assumed, averaged or normalized corneal vertex distance. The corneal vertex distance may also be a corneal vertex distance that has been determined beforehand via another measurement, which corneal vertex distance is individual to the user. The scaling factor for the frame plane of a spectacles frame worn by the user enables the conversion of the distances measured in the image of the user with the spectacles frame into corresponding "actual" distances in the frame plane. The scaling factor for the frame plane may be used to determine additional parameters, for example disc length, disc height, centering height, distance between the lenses, lens diameter etc. Additional corrections are possible via previous additional inputs of additional parameters, for example inclination, face form angle etc. These parameters may be average parameters. The parameters may also be determined otherwise, for example via already known measurement methods. The device may include corresponding parameter detection means to detect at least one parameter of the usage position of spectacles or of a spectacles frame worn by the user, for example inclination, face form angle and/or corneal vertex distance.

The device may comprise a parameter determination device which is designed to determine at least one optical parameter of at least one of the eyes of the user, and/or a parameter of the usage position of spectacles or of a spectacles frame in front of the eyes of the user, under consideration of the determined distance of the eye from the image capturing device. The at least one optical parameter may in particular be determined using the distances measured in the captured image and under consideration of the previously determined scaling factors.

The at least one optical parameter of the user may in particular be the monocular pupillary distance; and/or the interpupillary distance; and/or the disc length of spectacles or of a spectacles frame worn by the user; and/or the disc height of spectacles or of a spectacles frame worn by the user; and/or the centering height of spectacles or of a spectacles frame worn by the user; and/or the distance between the lenses of spectacles worn by the user or between the lens rings of a spectacles frame worn by the user; and/or the diameter of the lenses of spectacles worn by the user, or of the lens rings of a spectacles frame worn by the user; and/or the pupil diameter of one or both eyes of the user.

The above and further parameters of the user and/or of the usage position of spectacles or of a spectacles frame in front of the eyes of the user are described in DIN EN ISO 8624 and/or DIN EN ISO 1366 and/or DIN 58208 and/or DIN 5340, for example. The book, "Die Optik des Auges and der Sehhilfen" ["The optics of the eye and of vision aids"], by Dr. Roland Enders, 1995, Optische Fachveroffentlichung GmbH, Heidelberg, is also referenced with regard to the definition of the parameters of the eyes of a user or of the usage position of spectacles or of a spectacles frame in front of the eyes of the user. For terminology definitions, the standards as well as the cited book inasmuch represent an integral disclosure component of the present application.

The image capturing device may comprise a digital camera (a CCD camera, for example) that is directed toward the eye or eyes of the user. The image capturing device may also comprise additional optical components (for example lenses, mirrors, beam splitters etc.) in order to achieve a suitable beam bath, a suitable magnification etc.

In order to realize a type of stereo camera system, the image capturing device may be designed and set up to capture images of the specular reflection of the at least two different viewing angles or capture positions, wherein at least one image is captured per viewing angle or per capture position. If the image capturing device comprises a camera, this can be arranged such that it can rotate or pivot in order to capture images from at least two different perspectives. The image capturing device may also comprise at least two cameras that essentially simultaneously capture images from different viewing angles or from different capture positions.

Using the captured images, the eye-image capturing device distance may be determined for each of the viewing angles or for each of the capture positions. For each of the viewing angles or for each of the capture positions, the distance determination device may thus be designed to:

determine data with regard to the distance between the two predetermined points of the light reflection and the curvature of the at least one line-shaped segment of the light reflection in the at least one image captured from this viewing angle or from this capture position; and determine the distance of the eye from the image capturing device at this viewing angle or at this capture position using the determined data with regard to the distance between the two predetermined points of the light reflection and the curvature of the at least one line-shaped segment of the light reflection.

A change to the capture position may be determined via the determined distances of the eye or eyes from the image capturing device at different viewing angles. For this, the capture of a static object and the consideration of the angle of the optical axis of the image capturing device relative to the horizontal may additionally be used. The respective capture position may be determined from the eye-image capturing device distances in a horizontal projection plane. A stereo camera system or a stereoscopic measurement system may be realized from the at least two images captured from different viewing angles or capture positions. The horizontal plane may be the horizontal plane arranged in the reference system of the user and/or in the reference system of the Earth, and may travel through the center point of a pupil. This is especially the case if both eyes of the user are arranged at different heights (in the reference system of the Earth), for example.

The device may also comprise a 3D reconstruction device which is designed to determine, using the images captured from different capture positions and the determined distances of the at least one eye of the user relative to the image capturing device for each of the capture positions, spatial information in three-dimensional space for at least one point and/or one area of the at least one eye of the user and/or of spectacles or of a spectacles frame arranged in front of the eye. For example, three-dimensional spatial information for at least one of the following points may thus be determined:

for an intersection point of a horizontal plane in the reference system of the user with the spectacle lens edges and/or the spectacles frame edges of the spectacles, wherein the horizontal plane of the user intersects both pupils and travels parallel to a predetermined zero sight line of the user;

for an intersection point of a vertical plane in the reference system of the user with the spectacle lens edges and/or the spectacles frame edges of the spectacles, wherein the vertical plane of the user travels orthogonal to the horizontal plane of the user and parallel to the predetermined zero sight line of the user, and intersects a pupil of the user;

for at least one pupil center point;

for the borders of at least one spectacles lens of the user according to a dimensioning in a boxing system;

for the pupil center point of the spectacles frame of the spectacles.

What is understood by a dimensioning in the boxing system in the sense of this invention is the measurement system as it is described in relevant standards, for example in DIN EN ISO 8624 and/or DIN EN ISO 13666 DIN and/or DIN 58208 and/or DIN 5340.

Centering data and individual parameters of the user, for example the aforementioned optical parameters of the user, may be determined using the determined three-dimensional spatial information. Examples of devices and methods to determine centering data and individual parameters of the user in three-dimensional space are disclosed in patent applications DE 10 2005 003 699 A1 and DE 10 2014 015 671, for example.

The determination may include a determination of corresponding points in the acquired images from different capture positions or from different viewing angles. The corresponding points may be determined by means of a manual evaluation. The corresponding points may also be determined automatically for example using the method described in DE 10 2014 015 671.

The determined eye-image capturing device distance may also be used for further applications. The eye-image capturing device distance may thus be used as a parameter given a vision task which is shown on a screen (for example on the screen of a laptop, notebook, tablet, smartphone etc.) at a variable distance. In general, the eye-image capturing device distance may be used as a parameter given a variable depiction of arbitrary contents depending on the head position of the observer in front of a monitor etc.

The device may accordingly be a device to display arbitrary data or contents on the a monitor, wherein the monitor is arranged at a predetermined or known relative position. The device may comprise a monitor content determination device which is designed to determine the distance between the monitor and a user or an observer using the determined distance between the at least one eye of the user and the image capturing device. Using the "monitor-user" distance, the monitor content displayed or to be displayed on the monitor may be modified depending on the determined distance between the user and the monitor. For example, the size and/or the position of the images displayed on the monitor may thus be varied depending on the determined eye-image capturing device distance.

The device may also be a device for vision acuity determination with a monitor on which different optical test objects (optotypes) are displayed to perform a vision test. The distance of the user from the monitor may be determined depending on the determined eye-image capturing device distance (given a known relative arrangement of the monitor from the image capturing device). The individual nominal value of an optotype shown on the monitor may be determined depending on the determined eye-monitor distance. An example of a device for visual acuity determination with variable size of the optotypes is disclosed in the application DE 10 2014 009 459, for example.

The device may be designed as a portable, mobile device. The device may thereby be carried and operated in the hand of an operator. For example, for mobile use the objective of the image capturing device may be used as a fixed object for the user who views the objective in a zero viewing direction.

The device may in particular be integrated into a mobile computer (for example notebook, tablet, smartphone etc.). The camera integrated into the mobile computer thereby serves as an image capturing device. The calculations of the eye-image capturing device distance, of the scaling factor, of the optical parameters, of the location data in three-dimensional space etc. that are described above may be performed by means of the processor of the mobile computer. The lighting device may comprise at least one light source (for example a line light source) that is attached to the housing of the mobile computer and/or is integrated into the housing. It is also possible to use the monitor of the mobile computer as a light source. A combination of different light sources (for example monitor with additional light source(s)) is also possible.

The device may also comprise a memory to store the determined eye-image capturing device distance, and possibly of additional data (for example the determined optical parameters) and/or a data output device (comprising a monitor, for example) to output the determined eye-image capturing device distance, and possibly additional data. The distance determination device, the calibration data memory device, the scaling factor determination device, the parameter detection means, the parameter determination device, the 3D reconstruction device and/or the memory may be implemented in a data processing device comprising one or more processors or one or more computers.

A second aspect of the invention relates to a method comprising:

generation of a specular light reflection with at least one line-shaped segment on the cornea of an eye of a user, wherein the light reflection is generated by an illumination device which is arranged at a fixed relative position from an image capturing device;

capture of at least one image of the specular light reflection in the area of the cornea of the eye of the user;

determination of the distance between two predetermined or provided points of the light reflection and the curvature of the at least one line-shaped segment of the light reflection in the captured image; and determination of the distance of the eye of the user from the image capturing device using the determined data regarding the distance between the two predetermined or provided points of the light reflection and the curvature of the at least one line-shaped segment of the light reflection.

As described above, the light reflection may be generated by a structured light source having a previously known structure, arranged in the image capturing device. The previously known structure may in particular include a previously known distance between two predetermined points and a previously known shape (a straight line, for example) of an essentially line-shaped segment.

The method may also include a storage of the determined eye-image capturing device distance in a memory device; a display of the determined distance on a monitor; an acoustic reproduction of the determined distance; and/or a transmission of the determined distance to other devices etc. The determination of the distance between the two predetermined or provided points of the light reflection and the curvature of the at least one line-shaped segment of the light reflection in the captured image, and the determination of the distance of the eye of the user from the image capturing device using the determined data with regard to the distance between the two predetermined points of the light reflection and the curvature of the at least one line-shaped segment of the light reflection, may be executed by a suitably programmed processor or computer.

As described above, the determined distance may be determined under consideration of calibration data. For example, the method may comprise a detection of calibration data (for example via readout of data stored in a calibration data memory device) and a determination of the distance of the eye from the image capturing device under consideration of the calibration data. The calibration data may include data with regard to an association of distances between two predetermined points of the light reflection and of curvatures of the at least one line-shaped segment of the light reflection in the captured image at specific distances of the eye from the image capturing device.

As described above, the method may use differently designed or structured light reflections. The light reflection may thus have the shape of a light bar; and/or at least two point-shaped or circular areas; and/or multiple line-shaped segments.

The method may also include a determination of a scaling factor to recalculate a distance measured in an image captured by the image capturing device at an actual distance, and/or a determination of a scaling factor for the frame plane of a spectacles frame or of spectacles worn by the user using the determined distance of the at least one eye from the image capturing device.

The method may likewise include a determination of at least one optical parameter of at least one of the eyes of the user and/or of a parameter of the usage position of spectacles or of a spectacles frame in front of the eyes of the user under consideration of the determined distance of at least one eye from the image capturing device, as explained in the preceding in connection with the device.

The method may include a capture of images of the specular reflection in the area of the cornea of the eye of the user from at least two different capture positions. For each of the capture positions, the distance between two predetermined points of the light reflection and the curvature of the at least one line-shaped segment of the light reflection may be determined in the image captured from this capture position. The distance of the eye from the image capturing device may be determined at this capture position using the determined data with regard to the length and curvature of the at least one line-shaped segment of the light reflection. It is thus possible to create or generate stereoscopic images.

In particular, the method may include a determination of spatial information in three-dimensional space for at least one point and/or area of the at least one eye of the user and/or of spectacles or of a spectacles frame arranged in front of the eye, using the captured images from different capture positions and the determined distances of the at least one eye of the user from the image capturing device for each capture position.

The method may also include a determination of the distance between the user and a monitor using the determined distance between the at least one eye of the user and the image capturing device, wherein the monitor is arranged at a predetermined, known position relative to the image capturing device. The determined eye-monitor distance may be displayed to the user and/or be stored in a memory. The method may also include a modification of the monitor content displayed or to be displayed on the monitor depending on the determined distance of the at least one eye of the user from the image capturing device. For example, it is thus possible to realize a flexible method to determine optical vision properties or optical correction values of a user.

A third aspect relates to a computer program product comprising program parts which, if loaded in a computer, are designed to execute a method according to the second aspect and in particular the method steps explained in connection with the method according to the second aspect.

In particular, a computer program product comprising program parts is proposed, which program parts, if loaded into a computer, are designed to execute a method with the following steps:

detection of at least one image of the specular reflection of at least one light reflection in the area of the cornea of the eye of a user, wherein the light reflection has a line-shaped segment and is radiated from a lighting device which is arranged at a fixed relative position from an image capturing device;

determination of the distance between two predetermined points of the light reflection and of the curvature of the at least one line-shaped segment of the light reflection in the detected image; and determination of the distance of the eye of the user from the image capturing device using the determined data with regard to the length and curvature of the at least one line-shaped segment of the light reflection.

The eye-image capturing device distance may be determined simply and precisely with the device and the method according to the above aspects of the invention. In contrast to measurement devices—coincidence ophthalmometers, for example—in which the distance of light source from the cornea is either constrained as a constant via a technical device (by a Helmholtz-type collimator, for example) or, if imprecise knowledge leads to a measurement uncertainty (Javal-type), the distance is determined via measurement in the present design. No fixing of the user to be measured via a head support is thereby required. Rather, the measurement occurs in natural head and body position of the user. The device and the method are in particular suitable for mobile application. A mobile computer with integrated camera, and possibly additional light source, may thus be used as a measurement device. given mobile computers which have a monitor-side camera, the monitor itself may be used as a light source. The determined eye-image capturing device distance may be used to determine additional optical parameters of the user (for example interpupillary distance, the fitting height etc.). It is also possible to realize an improved stereo camera system. The determined eye-image capturing device distance may likewise be used to present contents depending on the position, in particular the head position of an observer, relative to a monitor. For example, the determined eye-image capturing device distance may thus be used as parameters given a vision task that is shown at variable distance on a tablet computer. Additional applications in camera-based optical systems are likewise conceivable.

BRIEF DESCRIPTION OF THE DRAWINGS/FIGURES

Figure 2:
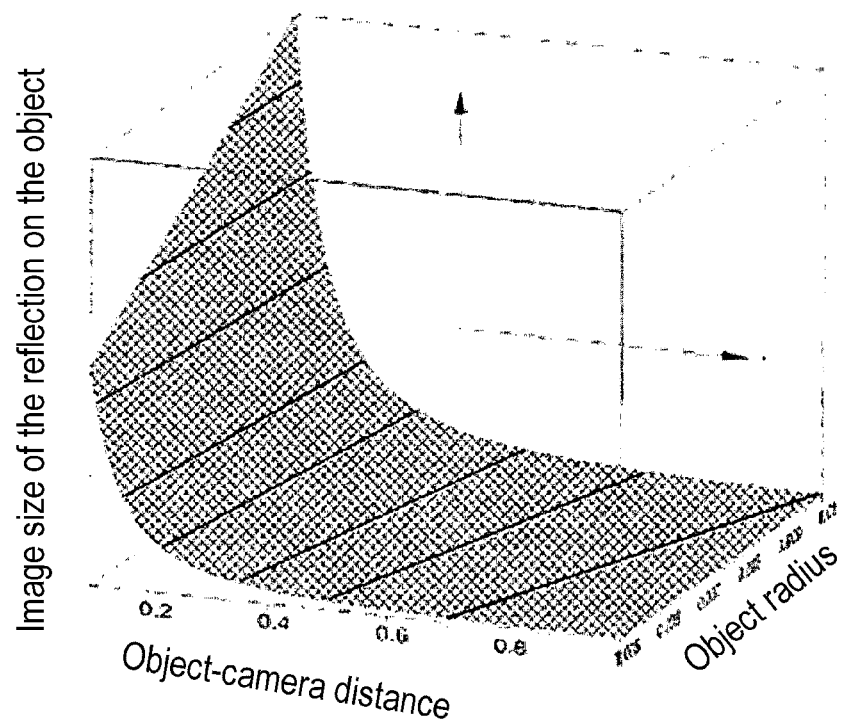
Figure 3:
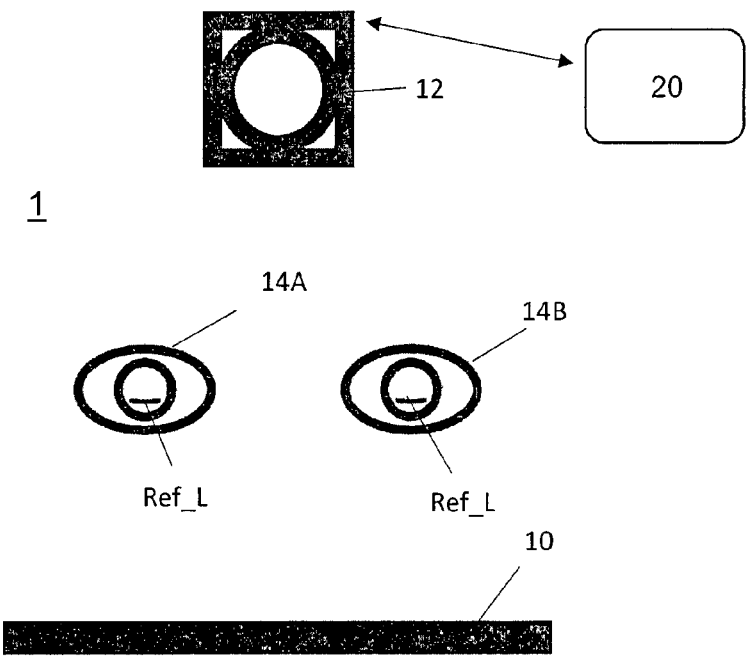
Figure 4:
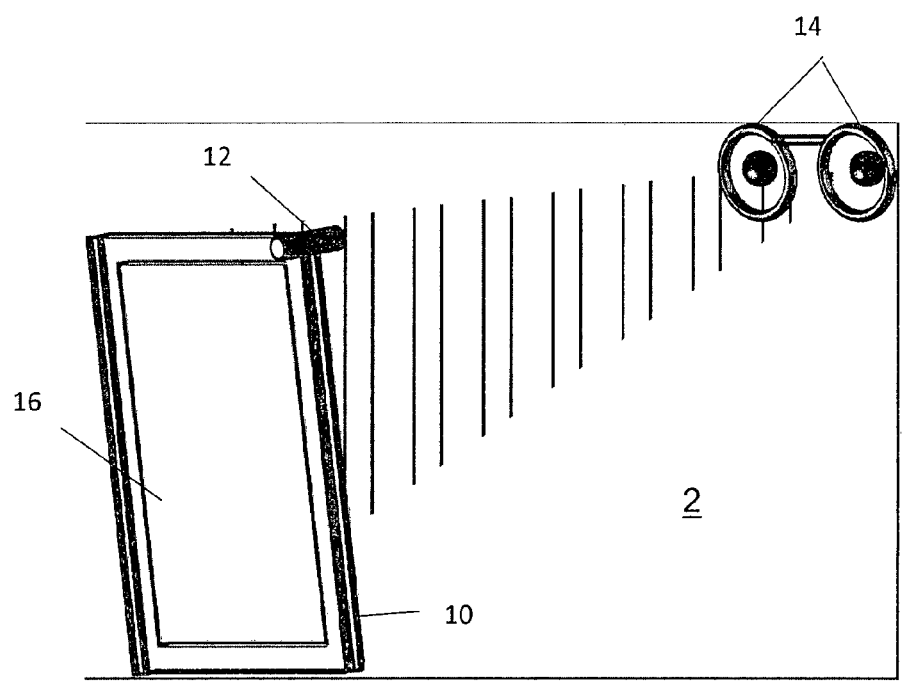
Figure 5:
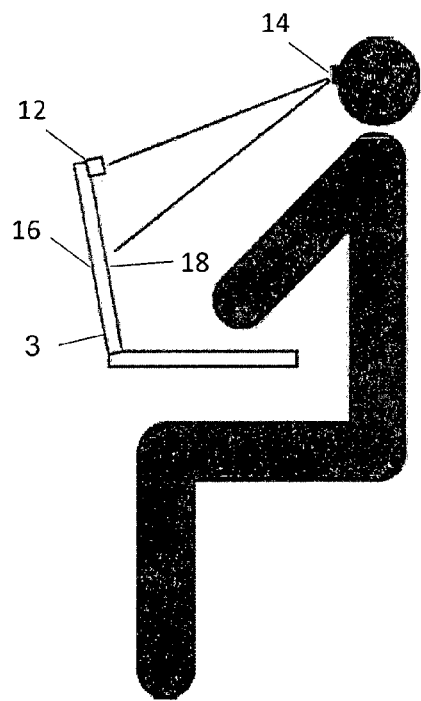
Figure 7:
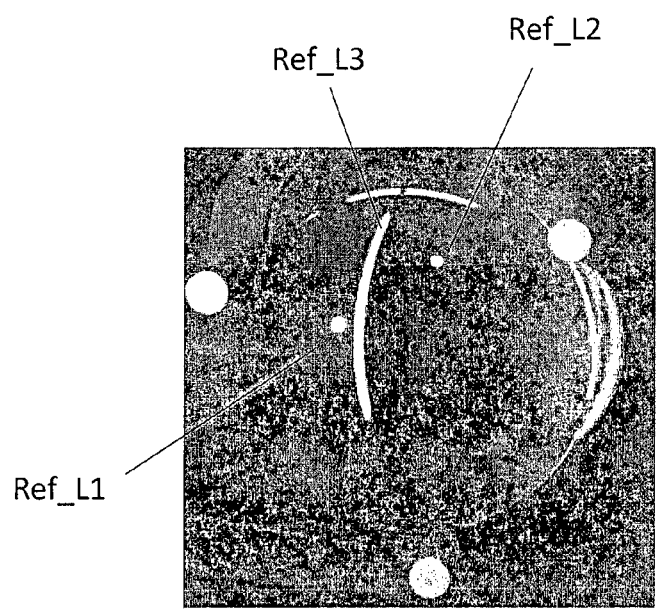
Figure 8:
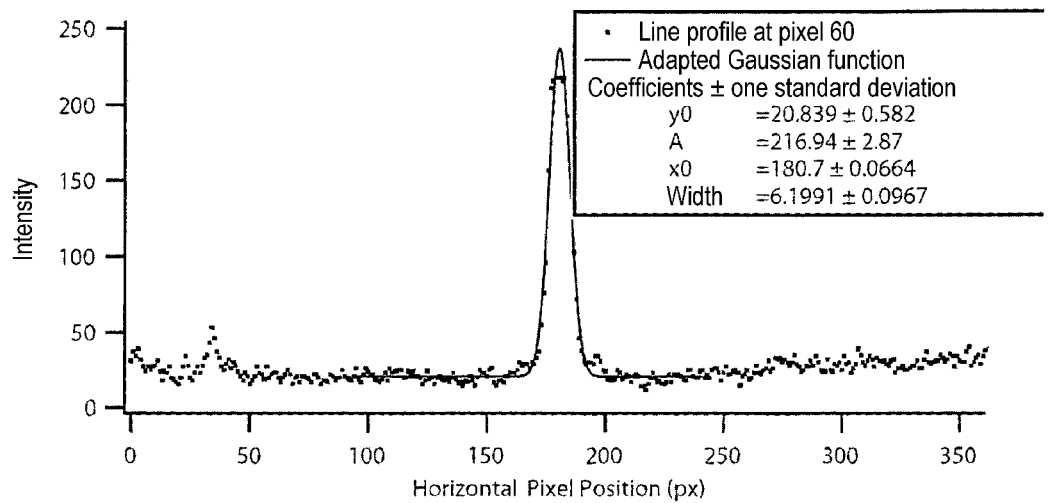
Figure 9:
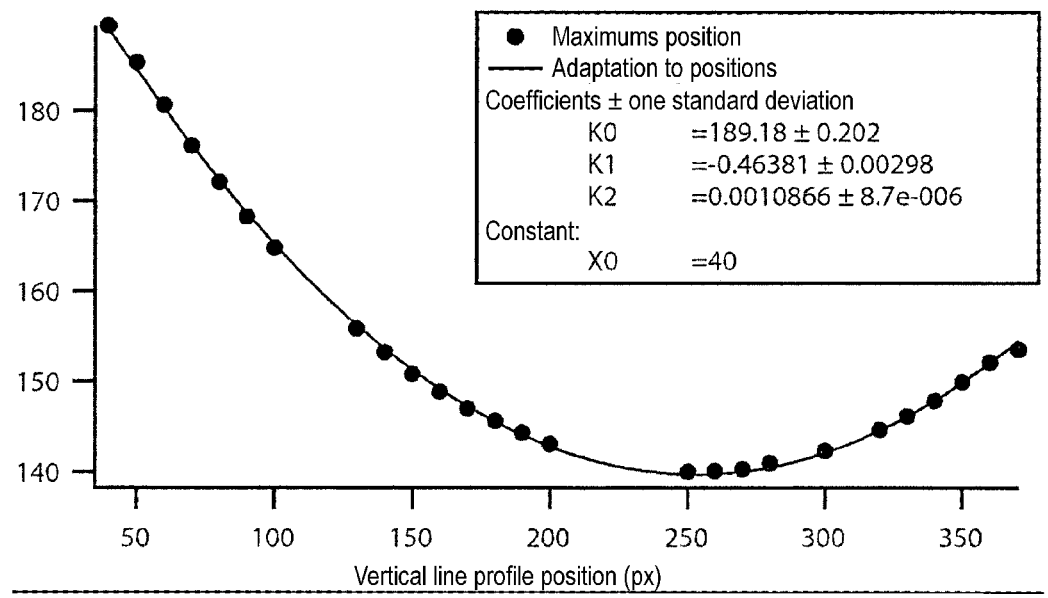
Figure 10:
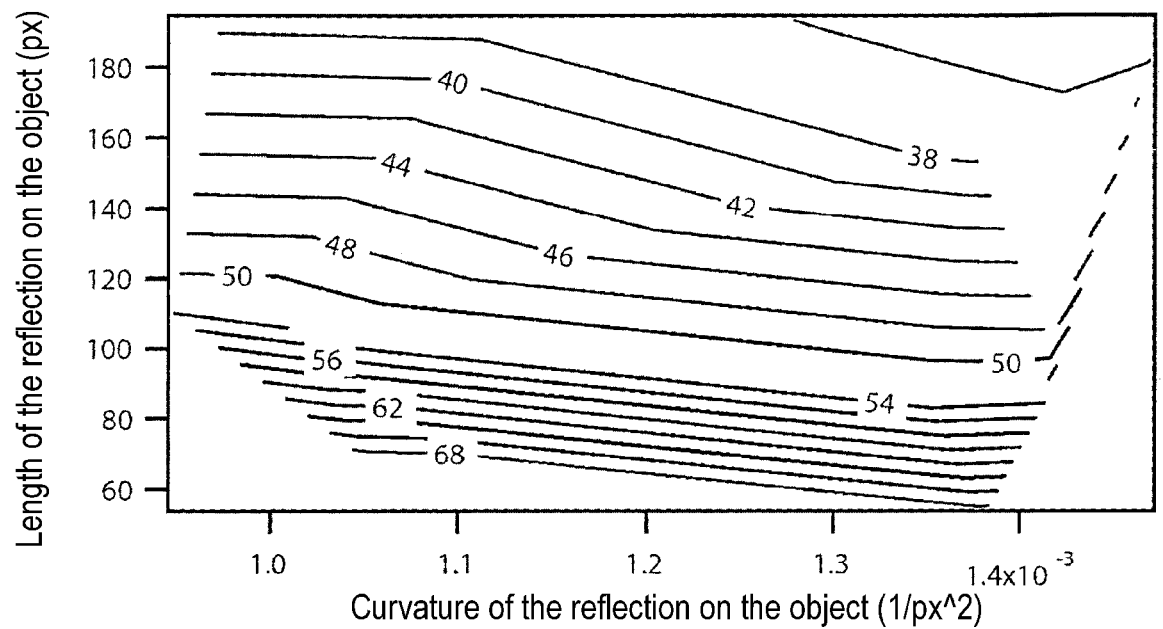
Figure 11:
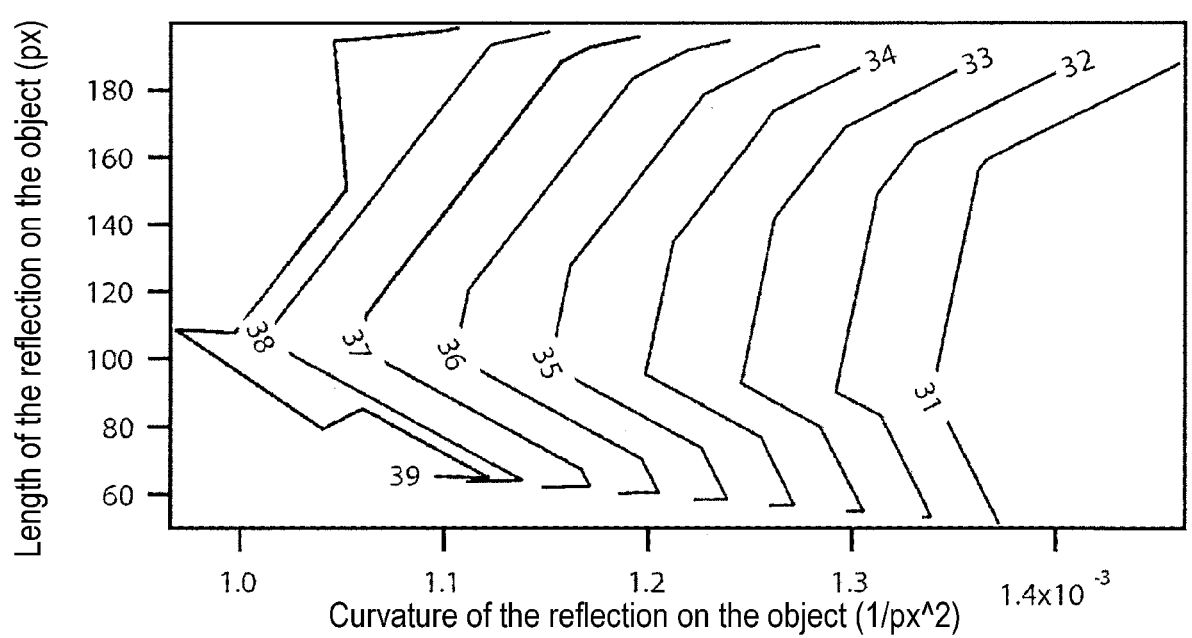
Figure 12:
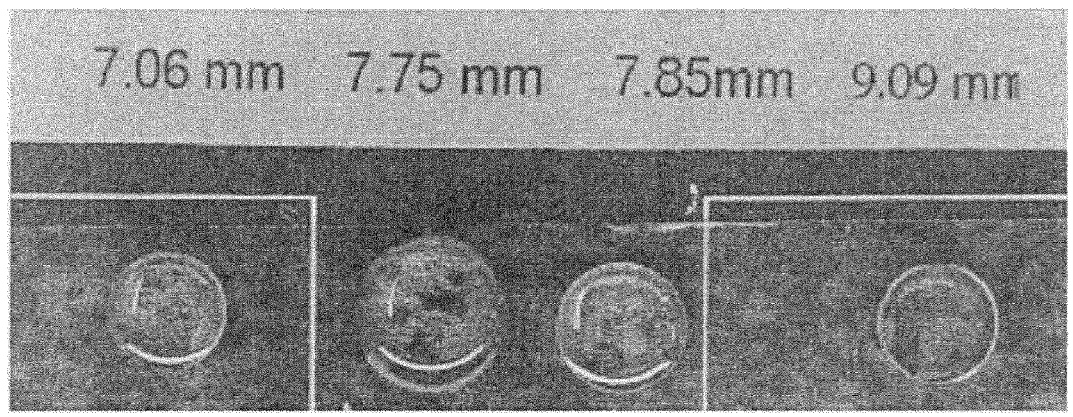
Figure 13A:
Figure 13B:
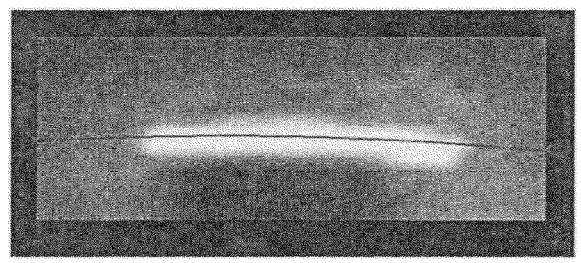

The invention is explained in detail in the following using examples of embodiments and accompanying drawings, Shown are:

FIG. 1 a schematic depiction of the measurement principle of the eye-image capturing device distance utilizing corneal reflection;

FIG. 2 in a three-dimensional diagram, the dependency of the measurement object-image capturing device distance on the object curvature and the size of the reflection image;

FIG. 3 a schematic depiction of a device with a camera and a measurement device to determine the eye-camera distance;

FIG. 4 a perspective, schematic depiction of a device having a camera and a measurement device to determine the eye-camera distance;

FIG. 5 a schematic depiction of a device having a camera and a measurement device to determine the eye-camera distance;

FIG. 6 examples of light sources;

FIG. 7 an example of an image exposure of a test object (a lens);

FIG. 8 an example of an intensity profile in a section through the light reflection in the image shown in FIG. 7B;

FIG. 9 the positions of the determined centers of the intensity profiles in different sections through the light reflection in the image shown in FIG. 7B, and an adapted quadratic function;

FIG. 10 isolines of the object-camera distance as a function of the shape of the specular light reflection on the cornea, measured in the image;

FIG. 11 isolines of the object curvature as a function of the shape of the specular light reflection on the cornea, measured in the image;

FIG. 12 image exposures of four different test objects;

FIG. 13A an example of an image of the eye area of a user;

FIG. 13B an example of an image of the specular light reflection of a line-shaped light source on the cornea.

DETAILED DESCRIPTION

FIG. 1 illustrates the measurement principle of a measurement system utilizing the corneal reflection. The measurement system comprises a camera (image capturing device) K and two point light sources L1 and L2 at a fixed position relative to these. The point-shaped light sources L1 and L2 are directed toward a reflective object O. In the image of the camera K, the object O is depicted and a specular reflex is generated by each light source. Given a flat object that moves at a fixed angle relative to the optical axis of the camera K, the distance of the light reflections of the two light sources is dependent on the distance of the object O from the camera K. Given a curved object, the distance of the light reflections likewise depends on the curvature of the object. Given a convex curvature that faces toward the camera K, the distance of the two light reflections relative to the one another decreases with increasing curvature.

The reflective object O has a curvature radius r. For example, the cornea of an eye thus acts like a spherical mirror with radius r.

For a spherical mirror, it applies in paraxial approximation that:

$$1/a'=1/a+2/r \quad (1)$$

Designated in Formula (1):

a' the distance between the vertex of the spherical mirror and the virtual image plane of the image of the light sources;

a the distance between the vertex of the spherical mirror and the plane in which the two point light sources L1 and L2 are arranged; and r the curvature radius of the spherical mirror.

The camera K is directed toward the object O. A connecting line between a diaphragm center point of the camera K and an object vertex point of the object O is shown as a dash-dot connecting axis A in FIG. 1 and may coincide with the optical axis of the camera K. Shown in FIG. 1 are the first distance y1 of the first light source L1 from the connecting axis A and the second distance of the second light source L2 from the connecting axis A. The two light sources L1 and L2 have a real distance $\Delta y = y2-y1$.

In the exposure of the object O produced by the camera K, the first virtual light image L1' of the first light source L1 appears at a first virtual distance y1' from the connecting axis A and the second virtual light image L2' of the second light source L2 appears at a second virtual distance y2' from the connecting axis A. The two virtual light images L1' and L2' are jointly situated in the virtual image plane in which they have a virtual image distance $\Delta y' = y2'-y1'$.

In the image plane of the camera K, the first light source image appears at the first image plane distance y1" from the connecting axis A, and the second light source image appears at the second image plane distance y2" from the connecting axis A. The two light source images thus have an image distance or an image size distance $\Delta y'' = y2''-y1'$ in the image plane of the camera K.

For the two light sources L1 and L2, it respectively applies that $$y1/(y1')=a/a' \quad (2)$$

$$y2/(y2')=a/a' \quad (3)$$

As viewed from the camera K, the distance of the images of the two light sources—thus the virtual image distance—is provided by:

$$\Delta y' = y2' - y1' \quad (4)$$

A solving of equations (1) through (3) for α' or y1' and y2' yields:

$$a' = (ar)/(2a+r) \quad (6)$$

$$y1' = a'y1/a \quad (7)$$

$$y2' = a'y2/a \quad (8)$$

An insertion of the formula (6) into formulas (7) and (8) yields:

$$y1' = y1r/(2a+r) \quad (9)$$

$$y2' = y2r/(2a+r) \quad (10)$$

For the virtual image distance Δy' of the two virtual light images L1' and L2' from one another, it thus applies that:

$$\Delta y' = y2' - y1' = (r(y2-y1))/(2a+r) \quad (11)$$

For an ideal camera, the image size Δy" of the virtual image distance Δy' of the reflection of the light sources is inversely proportional to the distance of the camera and proportional to the size of the virtual image distance Δy':

$$\Delta y'' \propto \Delta y'/(a'+a+b) \quad (12)$$

The distance b between the camera and the light source is known and fixed. in comparison to a, the distance a' is small and can be ignored. For b=0, it thus results that $$\Delta y'' \propto r(y1-y2)/(2a+r)a \quad (13)$$

Given a fixed real distance Δy=(y2−y1) of the light sources L1 and L2 from one another, and constant radius r of the object, the distance a may thus be determined from the image of the reflections of the two light sources, in particular from their image distance in the camera image, if a calibrated camera (for example a camera with fixed optics, in particular with a constant magnification factor) is used.

The obtained dependency of the distance a on the object curvature and the size of the reflection image for a fixed real distance Δy=(y2−y1) of the two light sources from one another is depicted in FIG. 2.

The above measurement principle can likewise be applied to line light sources, i.e. light sources which have extended, line-shaped and in particular straight-line segments. For example, the distance between the eye or the test object and the camera may be determined using the length and the curvature of the specular reflection of the line light source on the cornea of the eye or on the curved test object.

FIG. 3 schematically shows the design of an example of a device 1 having a camera 12 (as an image capturing device) and a measurement device to determine the distance of at least one of the eyes of a user from the camera (eye-camera distance). For example, the device 1 may be a device to determine the parameters of the eyes of a user and/or of the usage position of spectacles or of a spectacles frame in front of the eyes of a user; a video measurement and centering device (for example the ImpressionIST® device from the company Rodenstock GmbH, Germany); a device to display data (for example image data) depending on the position of an observer etc.

The device 1 comprises a lighting device having a line light source 10 that is designed and set up to generate a linear or essentially line-shaped light reflection on the cornea of the eyes 14A and 14B of a user. The device 1 also comprises an image capturing device having a camera 12 that is directed toward the eyes 14A and 14B of the user. For example, the line light source 10 may be a luminophore tube or an LED line lighting unit that is arranged at a fixed and previously known position relative to the camera 12. The camera 12 captures the reflections Ref_L of the light source on the cornea of both eyes. The reflection Ref_L appears curved in the image, wherein the curvature is dependent on the corneal radius given constant distance of the user from the camera. The curvature of the reflection Ref_L in the image is likewise dependent on the eye-camera distance, wherein this dependency is markedly less than the dependency on the corneal radius. The distance between the end points of the reflection Ref_L in the image (meaning the length of the reflection Ref_L in the image) is dependent on the eye-camera distance. The length of the reflection Ref_L is likewise dependent primarily on the eye-camera distance, and secondarily on the corneal radius.

The device 1 also comprises a distance determination device 20 that is designed to determine the distance of the respective eye from the camera 12 using the at least one captured image of the specular reflection of the light source. The distance determination device 20 may be realized by means of a suitably programmed computer or processor. The specular reflection of the light source on the cornea is designated as a specular light reflection.

FIG. 4 schematically shows a different example of a device 2 having a camera and a measurement device to determine the eye-camera distance, which device is suitable for mobile use. As given the device 1 shown in FIG. 3, the device 2 shown in FIG. 4 may be a device to determine the parameters of the eyes of a user and/or of the usage position of spectacles or of a spectacles frame in front of the eyes of a user; a video measurement and centering device; a device to display data (for example image data) depending on the position of an observer etc.

The device 2 may be integrated into a mobile computer, for example a laptop, notebook, tablet computer or smartphone. The device 2 comprises a camera 12 that, for example, may be the camera integrated into a mobile computer. The device 2 also comprises a line light source 10 that serves as a lighting device for the method for determining the distance of at least one eye of a user from the camera. The line light source 10 is arranged at a fixed and predetermined distance from the camera 12. The line light source 10 may, for example, be attached to the camera 12. The line light source 10 may, for example, be attached to the side of the housing of the mobile computer 16, which side is situated opposite the camera 12. Both the light source 10 and the camera 12 are directed toward the eyes 14 of the user. The specular reflection of the light source 10 on the cornea of the eyes 14 of the user is captured by the camera 12 and, as described above, is analyzed by means of the distance determination device (not shown) in order to determine the eye-camera distance.

It is possible to use the monitor 18 as a lighting device by displaying a suitable monitor content. In this instance, the light source is the diffusely radiated monitor content—for example in the form of a bright line—of a character with linear segment etc. on a black or homogeneously colored background. In this instance, the application of an additional light source is not required.

FIG. 5 shows an example of a device 3 which is integrated into a mobile computer 16 (for example in a notebook or a laptop PC) and/or is provided by the mobile computer 16, and which may be used to determine the distance of the eye or eyes 14 of a user from a camera 12 integrated into the mobile computer 16. In this instance, the monitor 18 of the mobile computer 16 serves as a lighting device. A light source shown on the monitor 18 radiates onto the cornea of at least one of the eyes 14 of the user. The specular light reflection on the cornea of the eye is captured by means of the camera 12 integrated into the mobile computer 16 and is analyzed by means of a distance determination device (not shown).

Figure 6A:
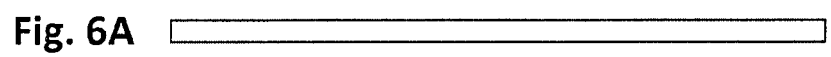
Figure 6B:
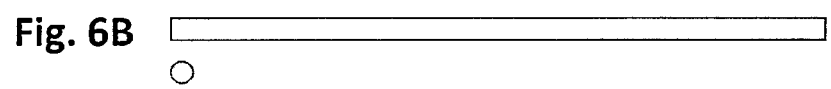

The light source may have different geometries, and thus may be designed as a structured light source. FIG. 6 shows four examples of light sources. FIG. 6A shows a linear light source in the form of a light bar having predetermined length. FIG. 6B shows a light source comprising a linear segment in the form of a light bar, and two point-shaped or circular segments at the two ends of the light bar (above and below the linear segment). The lighting device accordingly comprises a linear light source or line light source and two point-shaped light sources in a predetermined arrangement relative to one another that together form a structured light source. Since a localization of the middles or centers of the two point-shaped or circular segments in the captured image is more simply and precisely possible, a more precise distance measurement is enabled than with the light source shown in FIG. 6A.

Figure 6C:
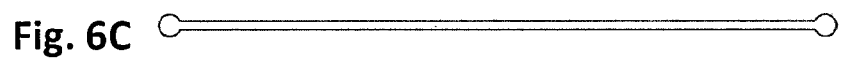
Figure 6D:
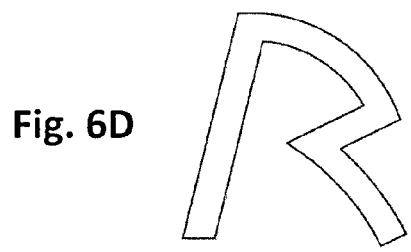

FIG. 6C shows a light source comprising a linear segment with ends executed in the shape of points or circles. An improved distance measurement is likewise enabled via the use of this light source. The advantage of this arrangement relative to the arrangement shown in FIG. 6B is that only a single light source is required. FIG. 6D shows a light source in symbolic form, here the corporate logo of the company Rodenstock GmbH. The light source has a linear or straight segment by means of which the described method may be implemented.

FIG. 7 shows a photograph of a curved lens having an example of a device that is designed and arranged similar to the devices 1, 2 and/or 3. The device thus has a camera and a measurement device comprising a line light source L3 and two point light sources L1 and L2, wherein the light sources L1, L2 and L3 are arranged at a fixed and previously known position (for example at a fixed distance) relative to the camera. Together, they form a structured light source of the lighting device. As an object with a spherical curvature with radius r which simulates the human eye, the curved lens captured in FIG. 7 serves as a test object or measurement object.

A light reflection Ref_L3 of the line light source L3 appears curved in the image of the camera K. Given constant distance of the object O from the camera K, the curvature is dependent on the radius r of the object O. The curvature of the light reflection is likewise dependent on the distance of the object O from the camera K. The distance of the light reflections Ref_L1 and Ref_L2 of the two point light sources L1 and L2 is dependent on the distance of the object O from the camera K, and on the curvature r of the object O (see also Equations 12 and 13). Since the dependency on the respective second cited variable is markedly less, an unambiguous relationship to the distance of the object O from the camera K and from the curvature r of the object O may be produced via combination of the two items of information from the reflections.

In particular, spherical silicate lenses having different radii of curvature may serve as test objects. Images of the various spherical silicate lenses are captured at different distances by means of the camera and evaluated by means of a data processing device (not shown).

FIG. 7 shows an example of an image capture of a lens having a curvature radius r=39.47 mm given a distance of 37 cm of the camera K from the object O. The light reflections of the three light sources are clearly visible in the captured image.

Using the image capture, the test object-camera distance may be determined by means of the distance determination device. The determination of the test object-camera distance includes a determination of the distance of the reflections Ref_L1 and Ref_L2 of the two point light sources L1 and L2 in the captured image. In order to determine the distance of the reflections Ref_L1 and Ref_L2 of the two point light sources L1 and L2 in the captured image, thus for example the image distance $\Delta y''$, the centers of the reflections of the respective point light source in the captured image may first be determined manually or automatically. The image distance $\Delta y''$ between the centers of the two reflections of the point light sources determined in the image (for example in pixels) is equal to the distance between the reflections in the image of the two point light sources. For example, the test object-camera distance may be determined from the image distance $\Delta y''$ by means of Equation (13).

The determination of the test object-camera distance also includes a determination of the curvature of the light reflection of the line light source L1 in the captured image. For the curvature of the light reflection of the line light source in the image, intensity or brightness profiles (line profiles) in the horizontal (or vertical) direction may be created across the area of the reflection in the image (for example with a width of 1 pixel (px)). Expressed in a different way, intensity or brightness profiles in different sections (for example different horizontal or vertical sections) may be determined via the light reflection of the light source in the image.

A Gaussian function or another suitable interpolation function may respectively be adapted to each of the determined intensity or brightness profiles. The maximum of the adapted Gaussian function indicates the center of the light reflection of the line light source L1 at the location of the respective line profile. A quadratic function whose factor for the quadratic dependency indicates the curvature of the line may be adapted via the determined centers of the line profile.

FIG. 8 shows an example of a line profile in a captured image of the corneal reflection of the line light source and the adapted Gaussian function. The horizontal position of an image point in pixels (px) is indicated as an abscissa, and the intensity or brightness of the image point (in greyscale values) is indicated as an ordinate. x0 thereby characterizes the highest point (thus the maximum) of the adapted Gaussian function, which is re-used as a center of the light reflection. In FIG. 8, y0 designates an intensity offset, A designates the amplitude, and "width" designates the width of the Gaussian distribution which does not need to be reused for the calculation.

FIG. 9 shows individual measurement values as well as a fitted function through the positions of the centers of the line profiles that are determined in the image. Via the fitted function, an adapted quadratic function is provided in which the pre-factor of the quadratic term, and thus the curvature, is designated as K2. K1 represents the linear coefficient, and K0 represents the constant of the adapted quadratic function. The curvature of the reflection Ref_R3 is therefore expressed by a function.

FIGS. 10 and 11 respectively show the isolines of the object-camera distances in cm (FIG. 10) and the object curvatures in mm (FIG. 11). The measured curvature of the light reflection of the line light source in the captured image (specified in $1/px^2$) is plotted on the abscissa of FIGS. 10 and 11. The measured distance of the light reflections of the two point light sources in the captured camera image in pixels (px) is plotted as the ordinate of FIGS. 10 and 11. From FIGS. 10 and 11, it is clear that the object curvature depends non-linearly on the object-camera distance. Both variables (object-camera distance and object curvature) may thus be determined unambiguously using the length and curvature of the light reflections of the light sources in the image.

A line light source is sufficient to determine the eye-camera distance. The determination may take place using the outermost points of the line light source. A simpler design may therefore be realized.

FIG. 12 shows photographs (image exposures) of four uncoated lenses with different curvature radii between 7 mm and 10 mm, namely 7.06 mm; 7.75 mm; 7.85 mm and 9.09 mm. The device with which the image exposures shown in FIG. 12 have been obtained corresponds essentially to the device 2 shown in FIG. 4.

In particular, the device has an essentially straight line light source which produces a curved, line-shaped light reflection on the examined lens. The line light source is attached to one of the long sides of a tablet computer. In this example, the length of the line light source is 55 cm, and the distance between the camera integrated into the tablet computer and the line light source is 18 cm. The curvature radii of the lenses are similar to the curvature radius of the human cornea (approximately 7.8 mm) and are thus suitable as test objects for the creation of calibration data for the device or the measurement device integrated into the device.

The lenses with the light reflections have been captured at different distances in the range of 20 cm to 75 cm from the camera. As described above, the curvature and the distance of the outermost points (thus the end points) of the light reflection of the line light source were determined or defined from the captured images.

A sole determination of the curvature or the length of the reflection may possibly allow only an imprecise determination of the distance of the object from the camera. If both curvature and length of the reflection are considered, the distance of the object (of an eye, for example) from the camera may be determined more precisely.

A length determination of the reflections of the light source in pixels may thereby have an error of at most 5% of the total length of the reflection of the light source, preferably of at most 2%, especially preferably of at most 1%.

Using the data with regard to the length and curvature of the light reflection in the image captured by the camera for different object-camera distances, and for objects with different curvatures, calibration data may be determined by means of which the object-camera distance and the curvature of an unknown measurement object (for example the eye of a user) may be determined. The calibration data may be stored in suitable form (for example tabular, functional etc.).

The calibration described above by means of calibration data which are acquired using exposures of corresponding test objects of various radii at various distances from the camera may be performed given all described devices and methods. More or fewer than four test objects may be used for this. The radii of the test objects and their distances from the camera may be chosen so that these essentially cover the area to be measured later. However, later measurements are also possible that exceed this area.

Using the data with regard to the length and curvature of the light reflection in the image captured by the camera, a scaling factor may be determined for different eye-camera distances and for objects with different curvatures, with which scaling factor the distances measured in the image may be converted into (real) eye-camera or object-camera distances. For example, a measurement of the interpupillary distance PD may be implemented with the calibration, or with this scaling factor.

The measurement of the interpupillary distance PD includes the capture of at least one image of the eye area of a user with the calibrated camera of the measurement system. FIG. 13A shows a captured image of the eye area of a user in a photograph.

The specular light reflection of the line light source may be identified manually or automatically in the captured image of the eye area, by means of suitable image processing algorithms. The image area which contains the specular light reflection of the respective light source may be excused from the image of the eye area and analyzed separately. FIG. 13B shows the excised image of the specular light reflection of the line light source.

Using the image data of the specular light reflection, the curvature and the length of the reflection of the line light source in the image may be determined manually or automatically by means of suitable image processing methods. The determination of the curvature of the specular light reflection may include the adaptation of quadratic function to the captured reflection. As described above, the quadratic function may be determined using line profiles in a plurality of horizontal or vertical sections through the light reflection.

In the example shown in FIGS. 13A and 13B, a parabola may be adapted with a quadratic factor. The quadratic pre-factor may be used as a curvature radius. The length of the reflection may be determined with sub-pixel accuracy from the image.

The position of the eye in space relative to the camera may be determined via a determination of the values for the object radius and the object-camera distance from the calibration (for example analogous to the diagrams shown in FIGS. 10 and 11). A determinable distance for the left eye and a determinable distance for the right eye thus result for the exposure shown in FIGS. 13A and 13B.

A conversion or scaling factor in pixels per millimeter [px mm$^{-1}$] results from the calibration for this eye-camera distance.

The pupil center of the respective eye may be determined manually or automatically by means of suitable image processing methods. A distance of the two pupil centers of, for example, 350 px results from the image exposure of the eye area (FIG. 13A), depending on the resolution of the exposure. An interpupillary distance PD in mm thus results under consideration of the previously determined scaling factor in px/mm Given a known fixed point relative to the camera, the interpupillary distance may be converted with the aid of an eye model for an infinite view. A convergence correction for the mean eye distance (as a mean value of the left and right eye distance) may thus be determined so that a corrected interpupillary distance results.

An improvement of the measurement accuracy may be achieved via a higher resolution of the image. This may be achieved via a smaller measurement interval or via use of an objective with smaller aperture angle. If the measurement device should be integrated into a mobile computer, a front-lens optic may be used for the camera. An improvement of the measurement accuracy may also be achieved via a different form of light source.

REFERENCE LIST

A connection axis
O object

K camera
L1, L2 point light sources
L3 line light source
Ref_L light reflection on the cornea
Ref_L1 reflection of a point light source on a test object
Ref_L2 reflection of a point light source on a test object
Ref_L3 reflection of a line light source on a test object
y1 first distance
y2 second distance
y1' first virtual distance
y2' second virtual distance
y1" first image plane distance
y2" second image plane distance
Δy real distance
Δy' virtual image distance
Δy" image distance
1, 2, 3 device
10 lighting device
12 image capturing device (a camera, for example)
14 pair of eyes
14A, 14B eyes
16 mobile computer
18 monitor
20 distance determination device

The invention claimed is:

1. A device for determining the distance of at least one eye of a user from one or more cameras, the device comprising:
a light source which is arranged at a predetermined relative position from the one or more cameras, and which is configured to generate, on the cornea of the eye of the user, at least one specular light reflection which has a line-shaped segment, the one or more cameras being configured to capture at least one image of the specular light reflection in the area of the cornea of the eye of the user; and
a distance determination device configured to:
determine data with regard to a distance between two predetermined points of the light reflection and the curvature of the at least one line-shaped segment of the light reflection in the captured image;
automatically locate the two predetermined points of the light reflection and the at least one line-shaped segment of the light reflection in the captured image; and
determine the distance of the eye from the one or more cameras using the determined data with regard to the distance between the two predetermined points of the light reflection and the curvature of the at least one line-shaped segment of the light reflection.

2. The device according to claim 1, further comprising:
a calibration data storage device configured to store calibration data,
wherein the calibration data include data with regard to an association of distances between (i) the two predetermined points of the light reflection and the curvatures of the at least one line-shaped segment of the light reflection in the captured image and (ii) determined distances of measurement objects from the one or more cameras, and
wherein the distance determination device is configured to determine the distance of the eye from the one or more cameras using the calibration data.

3. The device according to claim 1, wherein
the light reflection has the shape of one or more of (i) a light bar,
(ii) at least two point-shaped or circular regions, and (iii) multiple line-shaped segments.

4. The device according to claim 1, further comprising:
a scaling factor determination device which, using the determined distance of the at least one eye from the one or more cameras, is configured to determine at least one of (i)
a scaling factor to convert a distance measured in an image captured by the one or more cameras into an actual distance, and (ii)
a scaling factor for the frame plane of a spectacles frame or spectacles worn by the user.

5. The device according to claim 1, further comprising:
a parameter determination device configured to determine at least one optical parameter of the at least one eye of the user and/or at least one parameter of the usage position of spectacles or of a spectacles frame in front of the eyes of the user using the determined distance of the at least one eye from the one or more cameras.

6. The device according to claim 1,
wherein the one or more cameras are configured to capture images of the specular light reflection in the area of the cornea of the eye of the user from at least two different capture positions; and
wherein, for each of the capture positions, the distance determination device is configured to:
determine data with regard to the distance between two predetermined points of the light reflection and the curvature of the at least one line-shaped segment of the light reflection in the at least one image captured from this capture position; and,
use the determined data with regard to the distance between the two predetermined points of the light reflection and the curvature of the at least one line-shaped segment of the light reflection to determine the distance of the eye from the one or more cameras for this capture position.

7. The device according to claim 6, further comprising:
a 3D reconstruction device configured to determine, using the images captured from different capture positions and using the determined distances of the at least one eye of the user from the one or more cameras for each of the capture positions, spatial information in three-dimensional space for at least one point and/or area of the at least one eye of the user and/or of spectacles or of a spectacles frame arranged in front of the eye.

8. The device according to claim 1, further comprising:
a monitor which is arranged at a predetermined position relative to the one or more cameras, and
a monitor content determination device configured to:
determine the distance between the monitor and the user using the determined distance between the at least one eye of the user and the one or more cameras; and
modify the monitor content to be displayed on the monitor depending on the determined distance between the user and the monitor.

9. A method, comprising:
generating a specular light reflection having at least one line-shaped segment on a cornea of at least one eye of a user, wherein the light reflection is generated by a light source, light source being arranged at a fixed position relative to one or more cameras;
capturing at least one image of the specular light reflection in the area of the cornea of the eye of the user;
determining the distance between two predetermined points of the light reflection and of the curvature of the at least one line-shaped segment of the light reflection in the captured image;

automatically locating the two predetermined points of the light reflection and the at least one line-shaped segment of the light reflection in the captured image; and determining the distance of the eye of the user from the one or more cameras using the determined distance between the two predetermined points of the light reflection and the curvature of the at least one line-shaped segment of the light reflection.

10. The method according to claim 9, further comprising:
detecting calibration data which include data with regard to an association of distances between (i) two predetermined points of the light reflection and curvatures of the at least one line-shaped segment of the light reflection in the captured images and (ii) determined distances of measurement objects from the one or more cameras; and
determining the distance of the eye from the one or more cameras using the calibration data.

11. The method according to claim 9, wherein:
the light reflection has the shape of one or more of (i) a light bar,
(ii) at least two point-shaped or circular areas, and (iii) multiple line-shaped segments.

12. The method according to claim 9, further comprising:
determining a scaling factor for conversion of a distance measured in an image captured by the one or more cameras at an actual distance; and/or
determining a scaling factor for the frame plane of a spectacles frame or of spectacles worn by the user, using the determined distance of the at least one eye from the one or more cameras.

13. The method according to claim 9, further comprising:
determining at least one optical parameter of the at least one eye of the user and/or of a parameter of the usage position of spectacles or of a spectacles frame in front of the eyes of the user using the determined distance of the at least one eye from the one or more cameras.

14. The method according to claim 9, further comprising:
capturing images of the specular light reflection in the area of the cornea of the eye of the user from at least two different capture positions; and
for each of the capture positions:
determining the distance between two predetermined points of the light reflection and the curvature of the at least one line-shaped segment of the light reflection in the image captured from this capture position; and determining the distance of the eye from the one or more cameras at this capture position using the determined distance between the two predetermined points of the light reflection and the curvature of the at least one line-shaped segment of the light reflection.

15. The method according to claim 14, further comprising:
determining spatial information in three-dimensional space for at least one point and/or area of the at least one eye of the user and/or of spectacles or a spectacles frame arranged in front of the eye using the images captured from different capture positions and using the determined distances of the at least one eye of the user from the one or more cameras, for each capture position.

16. The method according to claim 9, further comprising:
determining the distance between the user and a monitor which is arranged at a predetermined relative position from the one or more cameras using the determined distance between the at least one eye of the user and the one or more cameras; and
determining monitor content to be displayed on the monitor, depending on the determined distance of the at least one eye of the user from the one or more cameras.

17. A non-transitory computer-readable medium having instructions stored thereon that, when executed by one or more processors, cause the one or more processors to:
detect at least one image of a specular light reflection in the area of a cornea of an eye of a user, the light reflection having a line-shaped segment, and the light reflection being generated by a light source that is arranged at a fixed position relative to one or more cameras;
determine the distance between two predetermined points of the light reflection and of the curvature of the at least one line-shaped segment of the light reflection in the acquired image;
automatically locate the two predetermined points of the light reflection and the at least one line-shaped segment of the light reflection in the captured image; and
determine the distance of the eye of the user from the one or more cameras using the determined distance between the two predetermined points of the light reflection and the curvature of the at least one line-shaped segment of the light reflection.

* * * * *